(12) United States Patent
Shoher et al.

(10) Patent No.: US 6,168,633 B1
(45) Date of Patent: Jan. 2, 2001

(54) COMPOSITE SURFACE COMPOSITION FOR AN IMPLANT STRUCTURE

(76) Inventors: Itzhak Shoher, PO Box 2127, Herzelia 46722 (IL); Aharon Whiteman, 13. J.L. Perez St, Petach Tikva (IL), 49206

( * ) Notice: Under 35 U.S.C. 154(b), the term of this patent shall be extended for 0 days.

(21) Appl. No.: 09/131,788

(22) Filed: Aug. 10, 1998

(51) Int. Cl.⁷ ...................................................... A61F 2/28
(52) U.S. Cl. .......................................... 623/23.6; 433/173
(58) Field of Search .................. 623/16.11, 23.6; 433/173, 174, 175

(56) References Cited

U.S. PATENT DOCUMENTS

| | | | |
|---|---|---|---|
| 4,027,392 | * | 6/1977 | Sawyer et al. ........................ 433/173 |
| 4,195,367 | * | 4/1980 | Kraus ...................................... 623/16 |
| 4,252,525 | * | 2/1981 | Child ..................................... 433/173 |
| 5,292,252 | * | 3/1994 | Nickerson et al. ................... 433/173 |
| 5,593,438 | * | 1/1997 | Akhavi et al. ............................ 623/6 |
| 5,759,205 | * | 6/1998 | Valentini .............................. 623/16 |
| 5,759,564 | * | 6/1998 | Milder et al. ......................... 424/426 |
| 5,770,255 | * | 6/1998 | Burrell et al. ......................... 424/2.1 |
| 5,837,275 | * | 11/1998 | Burrell et al. ....................... 424/409 |

* cited by examiner

*Primary Examiner*—Bruce Snow

(57) ABSTRACT

The implant of the present invention is composed of a core body having an outer surface of a composition of at least two dissimilar biocompatible metal components or metal alloy components in intimate contact with one another with said dissimilar metals or metal alloy components each having an EMF sufficient to form a potential difference of at least 25 mV and preferably over 100 mV.

8 Claims, 5 Drawing Sheets

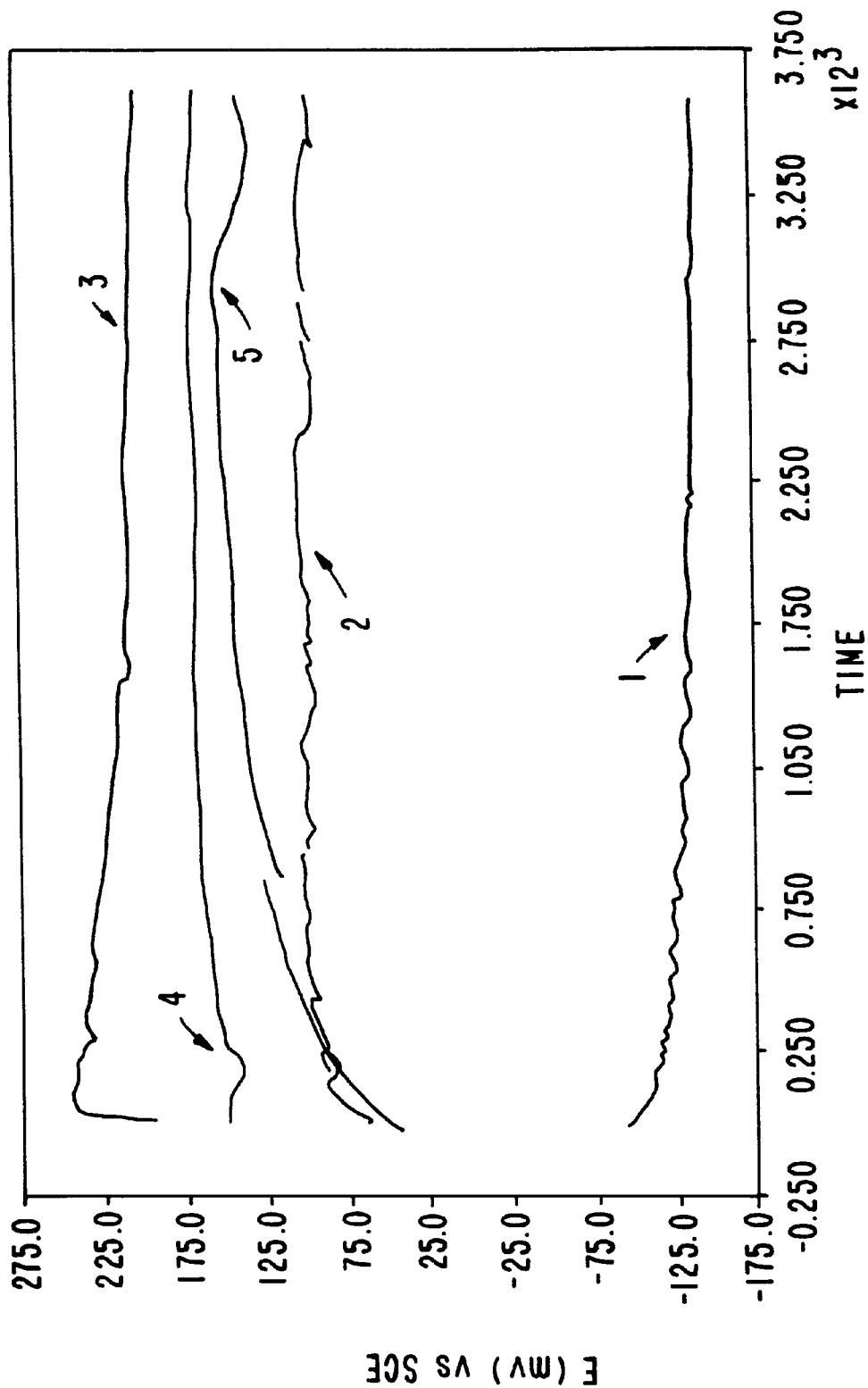

COMPOSITE SURFACE COMPOSITION FOR AN IMPLANT STRUCTURE

FIELD OF INVENTION

This invention relates to an implant structure for dental or medical use having a composite surface composition of a formulation for enhancing the stability of the implant and for stimulating bone growth upon being surgically inserted into bone.

BACKGROUND OF THE INVENTION

An implant is a prosthesis surgically implanted into skeletal bone. In dental applications the implant provides anchorage for the attachment of a dental restorative device. The dental implant is surgically inserted into a cavity formed in an edentulous region of the alveolar jawbone to become an integral part of the bone structure. Thereafter an abutment is attached to the implant in the preparation of a conventional dental restoration for use as a replacement of an extracted natural tooth. In medical applications the implant is typically used as an orthopedic appliance to repair or replace damaged skeletal parts and to stimulate fracture healing of bone. After the implant is surgically inserted a substantial healing period is required to assure bone growth and to permit clinical ossiointergration between the implant and bone. Factors which will affect assimilation of the implant in bone and the stimulation of new bone growth include the healing time period, the type of surgical procedure and the construction and composition of the implant. The implant must be composed of a biocompatible material and must provide sufficient strength for the intended dental or medical application. Conventional biocompatible materials used in the construction of the implant include stainless steel, titanium and their alloys. Titanium implants when surgically inserted into bone do not readily promote bone regeneration at the interface between the implant and bone and if a sufficient void exists microbial leakage and bacteria will accumulate leading to clinical failure of the implant.

SUMMARY OF THE INVENTION

It has been discovered in accordance with the present invention that the stability of an implant and its ability to stimulate bone growth particularly at the bone implant interface can be substantially enhanced by constructing the implant of a biocompatible material composition having an outer surface composed of at least two dissimilar biocompatible metal components or metal alloy components in intimate contact with one another. For purposes of the present invention each of the dissimilar metal components or metal alloy components forming the outer surface of the implant must possess an electromotive potential ("EMF") sufficient to provide a potential difference between the dissimilar metal components of above at least 25 mv and preferably above 100 mv. The dissimilar metal components must be in intimate contact and must surround at least part of the implant surface although it is preferable for the entire outer periphery of the implant to be composed of this composition. The outer surface composition of the implant should preferably include at least two or more dissimilar metals or metal alloy compositions of which at least 50% by weight are noble metals and preferably between 50–100% by weight constitute noble metals. The noble metals should be selected from the group consisting of gold, palladium, platinum and iridium with the balance of the dissimilar metal composition preferably selected from any of the elements in the 3rd or 4th column of the periodic table of elements. The electromotive potential difference of at least 25 mv, optimally above 100 mv, should exist between the dissimilar biocompatible metal components or metal alloy components. It should be understood that live bone is porous and that the fluid which permeates live bone is known to be electrolytic. In accordance with the present invention the existence of a composite surface of such dissimilar metals promotes bone integration and accelerates new bone growth at the interface between the implant and bone.

It is further contemplated in accordance with the present invention to include appropriate ceramic and/or non-metallic constituents in the surface composition of the implant to further stimulate bone growth.

BRIEF DESCRIPTION OF THE DRAWINGS

Other features and advantages of the present invention will become apparent from the following detailed description of the invention when read in conjunction with the accompanying drawings of which:

FIG. 8 shows a graphical plot of the potential of each of five different sample composites of dissimilar metal components in accordance with the present invention.

DETAILED DESCRIPTION OF A PREFERRED EMBODIMENT

Figure 1:
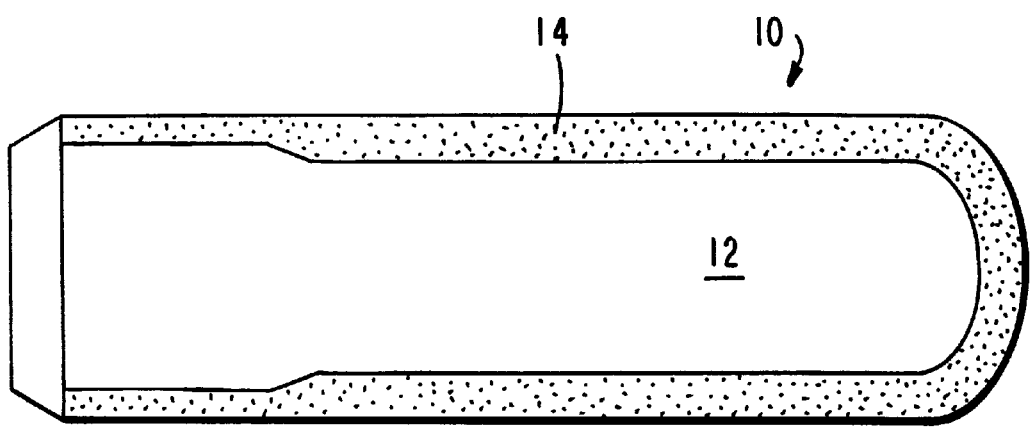
FIG. 1 is a cross sectional view of one embodiment of an implant in accordance with the present invention.

The invention will now be explained with reference to FIGS. 1–8 inclusive. In FIG. 1 an implant 10 is shown in cross section having a body 12 of a biocompatible material such as titanium and a surface coating 14 of a composite composition of at least two dissimilar conducting metals. The implant may have any desired geometry to facilitate surgical insertion into skeletal bone. It should be understood that although the formation of a surface coating 14 is preferred the entire implant may be fabricated from the composite material composition of dissimilar metals or metal alloys. It is also preferable but not essential to the present invention to have the surface coating 14 surround the entire outer surface of the implant body 12.

The surface coating 14 should be composed of at least two dissimilar biocompatible metal components or metal alloy components which are in intimate contact with one another and are electrically conductive. The distribution of the components on the surface of the implant can be homogeneous or non-homogeneous. The composition of each of the components can be of elemental metal(s) or of metal alloys and should include at least 50% by weight noble metals although between 50–100 weight % is preferred. The noble metals should predominantly be limited to one or more of the following metals: gold, palladium, platinum and iridium. The balance of the composition may include any or a combination of the elements in the 3rd or 4th column of the periodic table of elements. In addition the surface composition may include appropriate ceramic an/or non-metallic constituents which may react with the electrolyte to further stimulate bone growth and to provide other characteristics such as strength.

The surface coating 14 as above defined can be formed over the implant body 12 to provide different geometrical arrangements and to form various different surface patterns with different surface textures as will be illustrated in connection with FIGS. 1–7 inclusive. Moreover, the composition of the surface coating 14 may be formed starting with two or more metallic powder compositions pressed or sintered together or, alternatively, with one of the components part of a homogeneous matrix of the other component or with the components assembled as a laminated structure of various different layer compositions.

Figure 2:
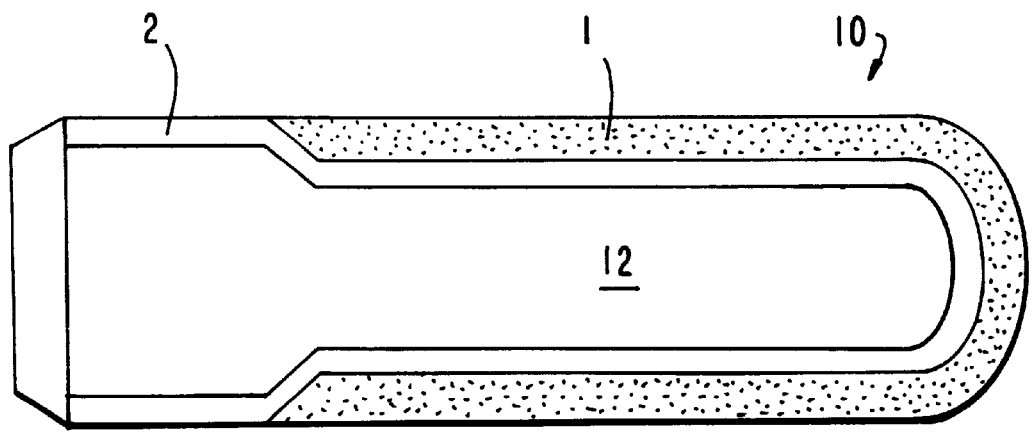
FIG. 2 is a cross sectional view similar to FIG. 1 using two different composite alloys on the external surface of the implant adjacent to one another.

In FIG. 1 a single coating of a surface composition 14 is shown surrounding an implant 10 with the surface composite composition 14 containing two or more of dissimilar metals or metal compositions in intimate contact with one another as explained heretofore with each of the dissimilar metals or metal compositions having an electromotive potential "EMF" sufficient to provide a potential difference between the metals or metal compositions of at least 25 mv and preferably over 100 mv. FIG. 2 is an example of an implant 10 coated with two separate surface composites 1 and 2 abutting one another. Each surface composite is of a composition of the elements of surface composition 14 as explained above so as to contain two or more dissimilar metals or metal alloys in intimate contact which will cause a potential difference of at least 25 mv to exist preferably between both the dissimilar metals or metal alloys in the composite as well as between the composite compositions 1 and 2 respectively. Stated otherwise, the potential difference can exist not only between the dissimilar metals in each composite composition 1 and 2 but also between the two composite compositions 1 and 2 respectively. The difference is composition between the surface composites 1 and 2 will provide a different EMF by a variation in the selection of dissimilar metals and their proportion to one another and may have a different surface pattern and surface texture.

Figure 3A:
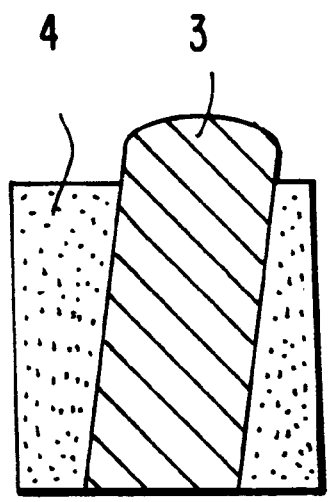
FIG. 3A shows an enlarged detail of a one section of the surface of FIG. 3.
Figure 3:
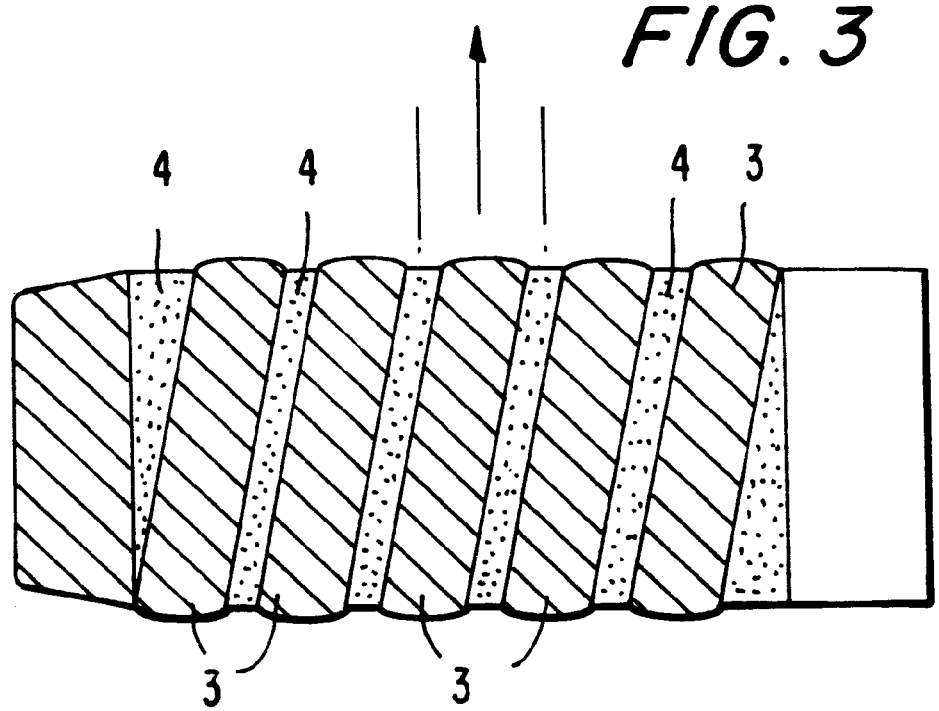
FIG. 3 is a diagrammatic view of another embodiment of an implant in accordance with the present invention composed of two different composite alloys in one preferred arrangement relative one another over the implant outer surface.

In FIG. 3 two different composite alloys 3 and 4 are separately coated over the implant 10 to form an arrangement in which the second coated alloy 4 forms layered bands of the alloy 4 separated from each other to expose the first coated alloy 3. The layered bands 4 may be uniformly spaced apart to expose sections of alloy 3 on each opposite side thereof as shown in FIG. 3a. Alternatively, the layered bands of the alloy 4 may be arranged in a continuous spiral configuration over the surface of alloy 3.

Figure 4B:
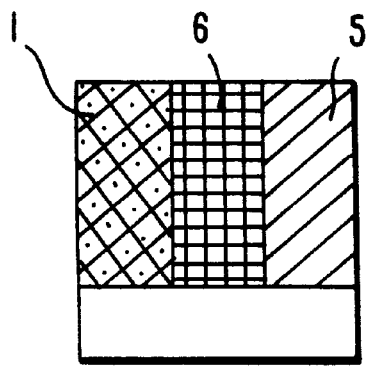
FIGS. 4A and 4B show various patterns for the surface composite composition of FIG. 4.
Figure 4A:
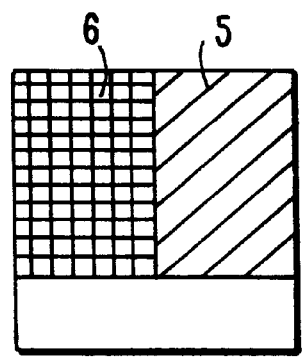
Figure 4:
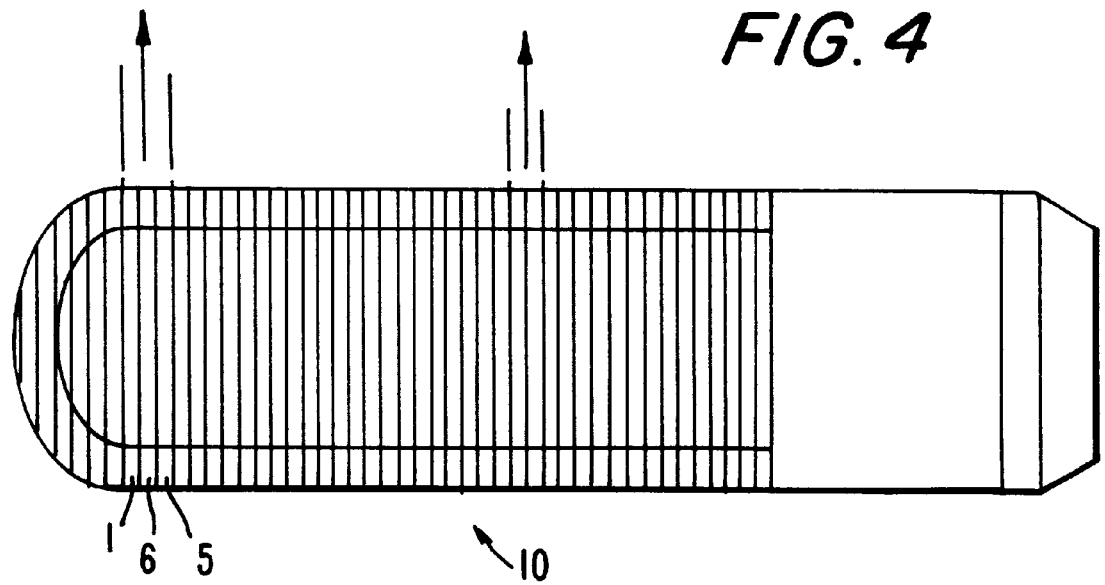
FIG. 4 shows an alternative surface geometry for the surface composite composition in accordance with the present invention.

In FIG. 4 the implant 10 is covered with a surface coating of three different layers of different composite alloys 5, 6 and 7 which are formed sequentially as adjacent layers such as by cladding etc. The surface patterns of each coating 5, 6 and 7 are different as evident in FIGS. 4a and 4b respectively.

The method of forming the surface composition 14 is not critical to the present invention and accordingly, any known technology for forming a coating may be employed including but not limited to: cladding, plating, thermal sintering, pressure sintering, plasma spraying, molten infiltration, or a combination thereof The coating technique used will strongly influence the particle sizes of the dissimilar coated metals and their topographical distribution and surface texture. In this regard there can be a homogeneous or non homogeneous distribution of the composite components on the surface of the implant. The particles of each composite component may vary in size from 0.1 micron to a few millimeters. Accordingly, each layer of a surface composite component may vary in thickness from 0.1 microns to a few millimeters.

Figure 5A:
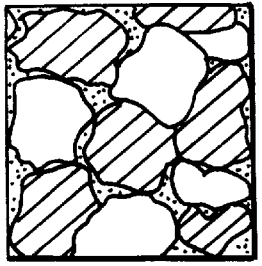
FIGS. 5A, 5B and 5C show different particle arrangements on the surface of the implant body in accordance with the present invention.
Figure 5B:
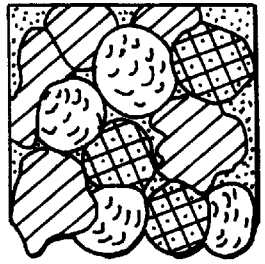
Figure 5C:
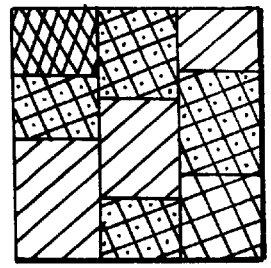
Figure 7A:
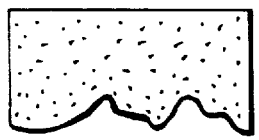
FIGS. 7A, 7B, 7C, 7D, 7E and 7F show different surface textures of the composites forming a variety of different surface cross-sectional patterns in accordance with the present invention.
Figure 7B:
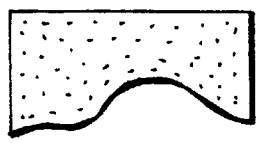
Figure 7C:
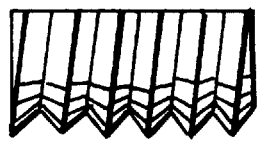
Figure 7D:
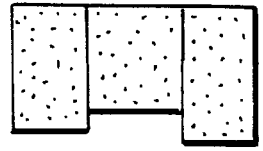
Figure 7E:
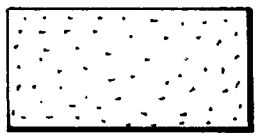
Figure 7F:
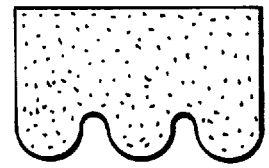
Figure 6:
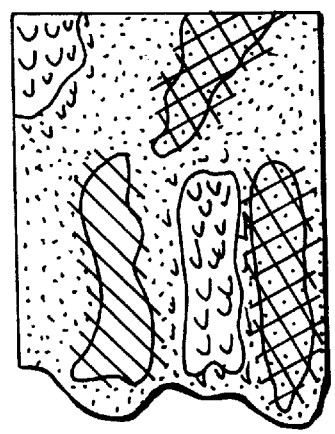
FIG. 6 is an illustration of a preferred surface morphology for the coated particles of the surface composite on the implant in accordance with the present invention.

FIGS. 5A–5C show different coated particle arrangements on the surface of the implant 10. It should be understood that the metal particles when coated should preferably have an irregular platelet like morphology as shown in FIG. 6 made up of one or more different metals in a metal or metal alloy matrix. FIGS. 7A–7F show various surface textures having different elevations in cross section which can be either inherently formed by the coating method used or by texturing the surface after coating. The texture at the surface of the implant may be smooth, rough, granular, grooved or hammered and may have any surface configuration and/or irregular surface geometry.

A free standing structure of a surface composite in accordance with the present invention can be formed from a mixture of dissimilar metals or metal alloys in particulate form which may then be compacted or pressure sintered into a desired geometrical shape. Additional layers can be coated over the surface as explained heretofore.

The following five separate specimen noble metal alloy compositions were tested to determine the level of EMF electromotive potential that could be generated from different alloy composition and to substantiate that the potentials would be substantially different from one another:

Specimen Alloy 98/1 is a homogeneous noble metal alloy of the following composition in wt %: gold-35%; palladium-32%; platinum-27%; iridium-4% and silver 2%.

Specimen Alloy 98/2 is a homogeneous noble metal alloy composition of the following composition in wt %: gold-65%; palladium-32%; ruthenium-2%; silver 0.5% other-0.5%.

Specimen Alloy 98/3 is a homogeneous noble metal alloy of the following composition in wt %: gold-94.5%; palladium-1.5%; silver-3% and copper 1.0%.

Specimen Alloy 98/4 is a homogeneous noble metal alloy composition of the following composition in wt %: gold-85%; palladium-4.7%; platinum-4.0%; silver 2.5%; other 0.3%; and Specimen Alloy 98/5 is a homogeneous noble metal alloy of the following composition in wt %: gold-97%; and silver 3%.

The determination of the EMF for each of the above alloy compositions relative to a reference electrode was based upon potentiodynamic anodic plots of the 5 alloys in a standard cell for electrochemical measurement. The use of this determination in a standard cell is the basis for determining the EMF of each dissimilar metal component in the surface composition 14 surrounding the implant 10 and may serve to calculate the minimum potential difference between the dissimilar metal components to establish the existence of a potential difference of at least 25 mv.

The standard cell was constructed to allow the insertion of a test electrode of the specimen alloy into a solution chamber, two auxiliary rod graphite electrodes, a Luggin capillary with salt bridge connection to a reference calomel electrode (SCE) and an inlet and outlet for inert gas and a thermometer. This standard electrochemical cell set up was used for testing each of the 5 alloys under conditions recommended by ASTM F746-94. The cell was kept at a constant temperature with a thermostat. The experimental procedure used was as follows:

1. The electrolyte solution used was 0.9% NaCl with a fresh solution used for each test.
2. The graphite auxiliary electrodes, salt-bridge and other components were placed in the test cell.
3. The temperature of the solution was brought to 37±1° C. by immersion in a controlled temperature water bath.
4. Prior to immersion of each test specimen the oxygen level in the solution was reduced by bubbling in argon for 0.5 hours.
5. The working electrode surface was prepared by wet grinding with 240 grit SiC paper and wet polishing with 66 grit paper and rinsed with deionized water and dried.
6. The test specimen was mounted on an electrode holder and placed into solution.
7. The cell was connected to a computer controlled potentiostat and the corrosion potential was measured for 1 hour after which time a potential scan was started. The current was continuously recorded while the potential was changed from corrosion potential up to +1V verses standard calomel electrode. It should be understood that the standard cell configuration used in the determination of the EMF for the metal component or metal alloy component selected in accordance with the present invention may be any conventional standard cell configuration.

The plots of potential verses time for each of the five specimen alloy compositions is shown in FIG. 8 and the steady state potential reached at the end of one hour after immersion in the electrolyte is shown in the following table:

TABLE

| Sample tested | EMF (at steady state) in mV |
| --- | --- |
| Specimen Alloy 98/1 | −136 |
| Specimen Alloy 98/2 | 98 |
| Specimen Alloy 98/3 | 197 |
| Specimen Alloy 98/4 | 174 |
| Specimen Alloy 98/5 | 147 |

The above table substantiates the level of EMF that can be generated in an electrochemical cell using different noble metal alloy compositions for the test electrode. To establish that a potential difference between dissimilar metal compositions can be developed in accordance with the present invention in a composite alloy another test was conducted in which a composite alloy was formed from particles of specimen alloy 98/4 in an amorphous matrix of specimen alloy 98/3. Particles of specimen Alloy 98/4 having the size of about 5 microns (thickness)×20 microns (average width)× 30 microns (average length) were alloyed in an amorphous matrix of specimen alloy 98/3. This composite alloy was then tested in the same electrolyte cell set up for each of the above specimen alloy compositions using the above described procedure. The EMF potential difference between the two components was found to be 23 mv (millivolts) when measured after one hour immersion in 0.9% NaCl in aqueous solution. To test the response of bone and soft tissue to an implant having a surface of this composition relative to a conventional metal implant the surface of a conventional implant was covered using this alloy composite and the implant inserted into a test animal. The results showed that the bone and soft tissue responded more positively against this surface relative to the conventional surface.

Further studies were conducted using two different implant surface compositions with the first represented by as composite alloy formed from particles of specimen alloy 98/2 in an amorphous matrix of specimen alloy 98/5. More specifically the particles of specimen alloy 98/2 were composed of flakes having a general particle size of 2 microns (thickness)×30 micron (average width)×80 micron (average length) which were alloyed in a matrix of specimen alloy 98/5. The two components were measured to form an EMF potential difference between the two components of 99 mv. A conventional implant having a surface composition of the above composite alloy was formed and tested in a animal. The bone and soft tissue response were found to be good around these implant surfaces. A second composite alloy of two components was formed from particles of specimen alloy 98/1 in an amorphous matrix of specimen alloy 98/5. The particles of specimen alloy 98/1 were flakes having a general particle size of 0.1 microns (thickness)×15 micron (average width)×35 micron (average length). The second composite alloy of two components formed an EMF potential difference between the two components of 283 mv. Once again a conventional implant having a surface composition of the above second composite alloy was formed and tested in a animal. The bone and soft tissue showed excellent responses adjacent this second composition. Based upon these results it is evident that the EMF between the dissimilar metal components should be at least 25 mv and preferably above 100 mv and optimally above 250 mv.

What we claim is:

1. An implant for stimulating and accelerating bone formation at the interface between the implant and bone comprising a core having at least two different surface compositions with the first and second surface compositions represented by a composite of multiple metal particles with the particles of the first surface composition being so small in size that a multiple number of particles exist in each square mm of surface area of said core and with said particles in said first surface composition having a geometry with an average length of less than 100 microns such that an EMF potential difference of at least 25 mv will be generated between said particles of said first and second composition in each square mm of the core surface area.

2. An implant as defined in claim 1 wherein the EMF potential difference between said first and second compositions is at least 100 mv.

3. An implant as defined in claim 2 wherein each surface composition on said core defines a coating covering at least a substantial part of the periphery of said core.

4. An implant as defined in claim 3 wherein each coating has a predetermined surface texture.

5. An implant as defined in claim 4 wherein said surface compositions define coatings of at least two composite formulations each of dissimilar metals or metal alloys in a laminated arrangement forming adjacent alternating layers in the form of bands spaced apart from one another along the outer periphery of the core.

6. An implant as defined in claim 5 wherein said at least one surface composition is composed of at between 50–100% by weight noble metals or metal alloys.

7. An implant as defined in claim 6 wherein said noble metals are selected from the group consisting of gold, palladium, platinum and iridium.

8. An implant as defined in claim 7 wherein the balance of said surface composition is composed of metals selected from the 3rd and 4th column of the periodic table of elements.

* * * * *